United States Patent
McNair

(10) Patent No.: US 11,948,691 B1
(45) Date of Patent: *Apr. 2, 2024

(54) PREDICTING ADDICTION RELAPSE AND DECISION SUPPORT TOOL

(71) Applicant: CERNER INNOVATION, INC., Kansas City, KS (US)

(72) Inventor: Douglas S. McNair, Seattle, WA (US)

(73) Assignee: Cerner Innovation, Inc., Kansas City, KS (US)

(*) Notice: Subject to any disclaimer, the term of this patent is extended or adjusted under 35 U.S.C. 154(b) by 0 days.

This patent is subject to a terminal disclaimer.

(21) Appl. No.: 17/378,245

(22) Filed: Jul. 16, 2021

Related U.S. Application Data

(63) Continuation of application No. 15/719,151, filed on Sep. 28, 2017, now Pat. No. 11,069,446.

(60) Provisional application No. 62/401,160, filed on Sep. 28, 2016.

(51) Int. Cl.
*G16H 50/30* (2018.01)
*G06F 17/18* (2006.01)

(52) U.S. Cl.
CPC ............. *G16H 50/30* (2018.01); *G06F 17/18* (2013.01)

(58) Field of Classification Search
CPC ........ G16H 10/20; G16H 70/20; G16H 70/60; G06F 19/30; G06F 19/32; G06F 19/324; G06F 19/325; G06F 19/326; G06F 19/34; G06F 19/36; G06Q 50/22; G06Q 50/24
USPC .......................................................... 705/2
See application file for complete search history.

(56) References Cited

U.S. PATENT DOCUMENTS

| | | | |
|---|---|---|---|
| 11,069,446 B1 | 7/2021 | Mcnair | |
| 2011/0137851 A1* | 6/2011 | Cavet | G01N 33/53 703/2 |
| 2016/0063402 A1* | 3/2016 | Webb | G06Q 10/063 705/348 |

(Continued)

FOREIGN PATENT DOCUMENTS

WO    2016/178617 A1    11/2016

OTHER PUBLICATIONS

Chih, Ming-Yuan et al. "Predictive modeling of addiction lapses in a mobile health application." Journal of substance abuse treatment vol. 46,1 (2014): 29-35. (Year: 2014).*

(Continued)

*Primary Examiner* — Devin C Hein
(74) *Attorney, Agent, or Firm* — Kilpatrick Townsend & Stockton LLP

(57) ABSTRACT

Technologies are provided for determining an individual's likelihood of relapsing into prior behavior subsequent to a treatment for a mental health or addiction disorder, and in some instances predicting a likelihood time frame for such a relapse. Target subjects having a risk of addiction relapse, non-adherence to a treatment program, or absconding, may be automatically identified based on a multiplicative-regression model for relative survival (MRS) that is developed for predicting risk or likelihood of relapse or non-adherence. Further, in some embodiments, a leading indicator of near-term future abnormalities may be provided thereby proactively notifying supervisory personnel responsible for the person and providing such personnel with timely notice to enable effective corrective, preventive, or trend-modifying maneuvers to be undertaken.

12 Claims, 11 Drawing Sheets

(56) References Cited

U.S. PATENT DOCUMENTS

2020/0071766 A1* 3/2020 Stefan ................. C12Q 1/6886

OTHER PUBLICATIONS

Tibshirani, R. "The lasso method for variable selection in the Cox model." Statistics in medicine vol. 16,4 (1997): 385-95. (Year: 1997).*
George, Brandon et al. "Survival analysis and regression models." Journal of nuclear cardiology: official publication of the American Society of Nuclear Cardiology vol. 21,4 (2014): 686-94. doi:10.1007/s12350-014-9908-2 (Year: 2014).*
Chih et al., "Predictive Modeling of Addiction Lapses in a Mobile Health Application", Journal of substance abuse treatment vol. 46, Issue 1, Available online at: <https://doi.org/10.1016/j.jsat.2013.08.004>, Jan. 2014, pp. 1-17.

* cited by examiner

```
##########################################################################

#  PLOT ROC

#################################################################### library(pROC)

ds4 <- read.csv(file="C:/0_cerdsm/IP/gaps_multiplicative_relative_survival_relapse_multi/
roc.csv")
roc1 <- roc(ds4[,1] ~ ds4[,2], percent=TRUE,
# arguments for auc
  partial.auc=c(100, 0), partial.auc.correct=TRUE,
  partial.auc.focus="sens",
# arguments for ci
  ci=TRUE, boot.n=100, ci.alpha=0.9, stratified=FALSE,
# arguments for plot
#  auc.polygon=TRUE, max.auc.polygon=TRUE,
  plot=TRUE, grid=TRUE, print.auc=TRUE, show.thres=TRUE)
sens.ci <- ci.se(roc1, specificities=seq(0, 100, 5))
plot(sens.ci, type="shape", col="lightblue")
plot(sens.ci, type="bars")

roc(ds4[,1] ~ ds4[,2], ds4, plot=TRUE)

# column-major
dsm <- matrix(c(128,12,23,245), ncol=2)
fisher.test(dsm)
```

*FIG. 3D.*

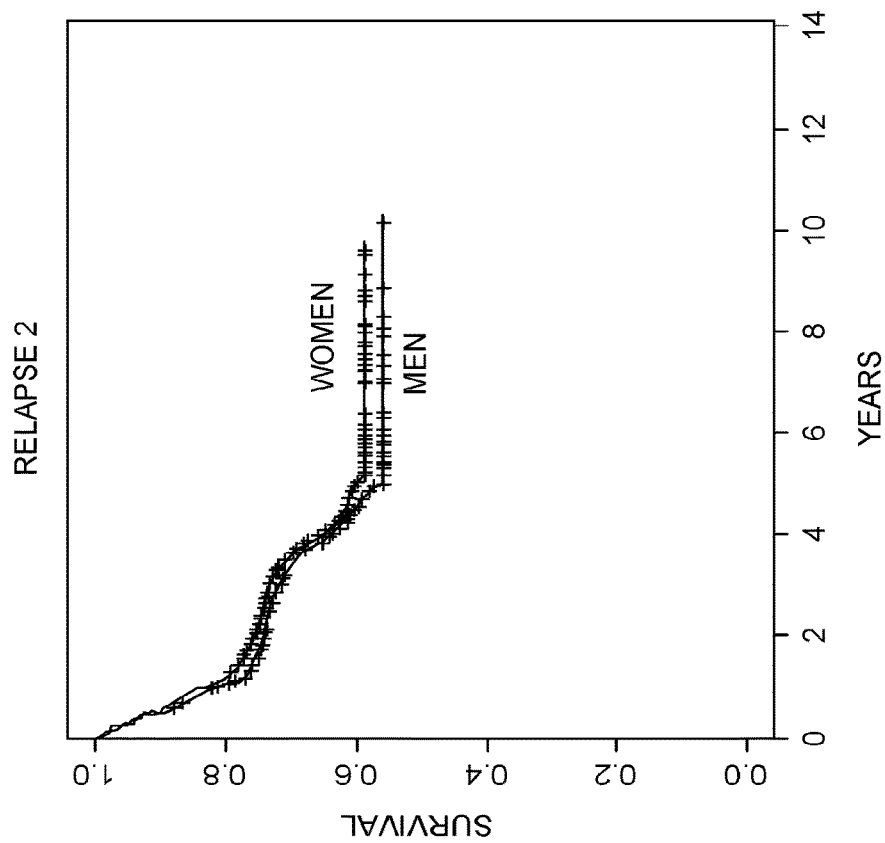
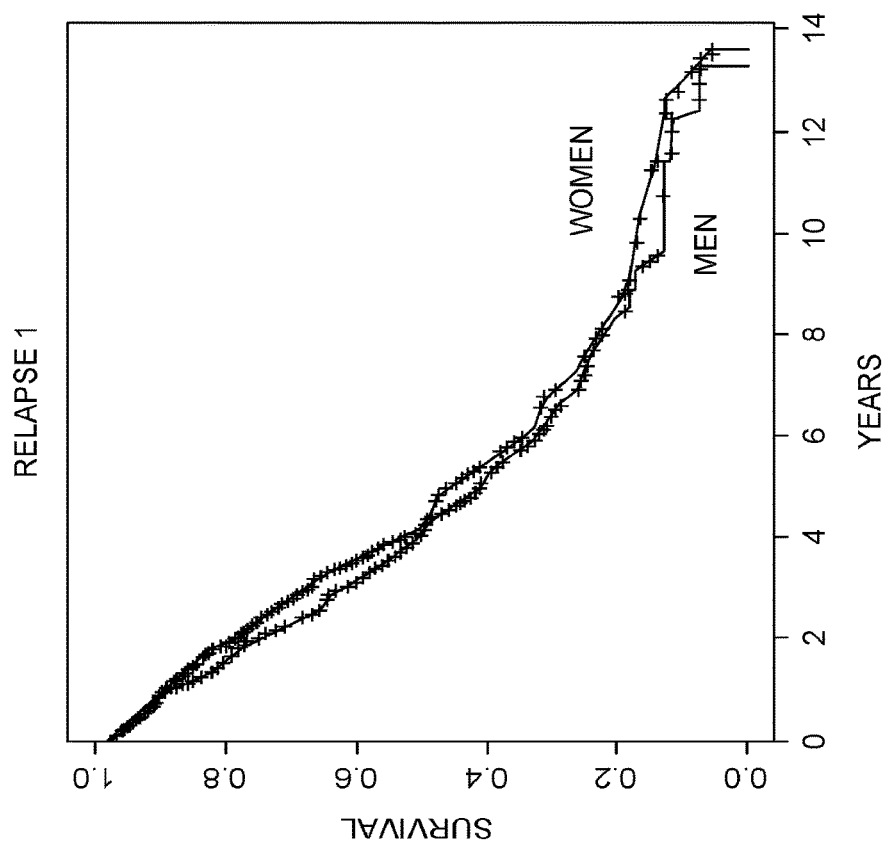
FIG. 4A.
FIG. 4B.

Example Manager User Interface – Alcohol dependency & relapse

| PATIENT IN TREATMENT FOR RELAPSE OF ALCOHOL DEPENDENCY... | | |
|---|---|---|
| • AGE | 66 | YEARS |
| • DELAY IN SEEKING TREATMENT FOLLOWING RELAPSE 1 | 30 | DAYS |
| • ADEQUATE PARTICIPATION IN CBT DURING PRIOR TREATMENT? (Y/N) | NO | |
| • TIME TO RELAPSE 1 | 95 | DAYS |
| • TIME HORIZON T FOR PREDICTING RELAPSE 2 | 365 | DAYS |

| EVALUATE | RESULTS |
|---|---|
| DATA COMPLETE? | YES |
| BASE COX PH MODEL PREDICTED PROBABILITY OF RELAPSE2 IN T DAYS | 46% |
| MRS MODEL PREDICTED PROBABILITY OF RELAPSE 2 IN T DAYS | 94% |
| INITIATE INTENSIFIED RELAPSE-PREVENTIVE ORDERSET? | YES |

*FIG. 5.*

```
############################################################################

# multiplicative relative survival relapse modeling for 2 consecutive relapses (r1 and r2) in
# addiction rehab treatment

###################################################################### traditional survival models involving merging r1 and r2 data. Nevertheless, one can notice two
important limitations of these traditional approaches.

# 1. the comparisons of risk factors between both groups would imply testing all the interactions
# with intervention rank.

# 2. second intervention-specific explanatory variables (time to relapse after first intervention,
# CBT_participation_p, time-before-reintervention, etc.) cannot be included, since they are
# missing for first-rank cases.  MRS techniques can handle these.

library(survival)
library(mvtnorm)
library(MRsurv)

# load data
r1 <- read.csv(file="c:/0_cerdsm/IP/gaps_multiplicative_relative_survival_relapse_multi/
relapse1.csv", header=TRUE,
        colClasses=rep("integer",5))

r2 <- read.csv(file="c:/0_cerdsm/IP/gaps_multiplicative_relative_survival_relapse_multi/
relapse2.csv", header=TRUE,
        colClasses=rep("integer",8))

# t      post-intervention follow-up time (in days).
# cens   relapse event at the end of the follow-up interval (1 for relapses and 0 for right-censoring).
# age    age group (ages 0 - 19 = 0; ages 20 - 39 = 1; ages 40 - 59 = 2; age 60+ = 3).
# male   gender (1 for men and 0 for women).
# delay  time in registry between relapse onset and start of second intervention (1 for more than
3 months and 0 otherwise).
# cbt    adequate participation in cognitive behavioral therapy after first intervention (1 for yes
and 0 otherwise).
# tr1    time to first relapse after first intervention (in days).

# generate Kaplan-Meier survival curves
fit1 <- survfit(Surv(t, cens) ~ male, data=r1)
fit2 <- survfit(Surv(t, cens) ~ male, data=r2)

plot(fit1, mark.time=FALSE, xscale=365.25, xlab='Years', ylab='Survival')
lines(fit1[1], lwd=2, xscale=365.24) # darken the first curve and add mark plot(fit2, mark.time=FALSE, xscale=365.25, xlab='Years', ylab='Survival')
lines(fit2[1], lwd=2, xscale=365.24) # darken the first curve and add mark
                                .
                                .
                                .
```

CONTINUES IN FIG. 6B

FIG. 6A

CONTINUES FROM FIG. 6A

.
.

```
# compute Cox model time-to-relapse from first intervention
cox.r1 <- coxph(Surv(t, cens) ~ age + male, data=r1)
summary(cox.r1)
#   n= 1031, number of events= 598 (58%)

#         coef exp(coef) se(coef)     z Pr(>|z|)
# age   0.17280  1.18862  0.08702  1.986  0.0471 *
# male -0.05342  0.94798  0.08482 -0.630  0.5288
# ---

#       exp(coef) exp(-coef) lower .95 upper .95
# age      1.189     0.8413    1.0022    1.410
# male     0.948     1.0549    0.8028    1.119

# Concordance= 0.537  (se = 0.012 )
# Rsquare= 0.004   (max possible= 0.999 )
# Likelihood ratio test= 4.34  on 2 df,  p=0.114
# Wald test          = 4.49  on 2 df,  p=0.1058
Score (logrank) test = 4.49  on 2 df,  p=0.1057 compute Cox model time-to-relapse from second intervention
cox.r2 <- coxph(Surv(t, cens) ~ age + male, data=r2)
summary(cox.r2)
#   n= 408, number of events= 140 (34%)

#         coef exp(coef) se(coef)     z Pr(>|z|)
# age   0.77764  2.17634  0.16481  4.719 2.38e-06 ***
# male -0.07307  0.92954  0.17334 -0.422   0.673
# ---

#       exp(coef) exp(-coef) lower .95 upper .95
# age     2.1763    0.4595    1.5756    3.006
# male    0.9295    1.0758    0.6618    1.306

# Concordance= 0.581  (se = 0.024 )
# Rsquare= 0.046   (max possible= 0.979 )
# Likelihood ratio test= 19.07  on 2 df,  p=7.233e-05
# Wald test          = 22.28  on 2 df,  p=1.453e-05
Score (logrank) test = 23.07  on 2 df,  p=9.762e-06 compute multiplicative relative models (r2 compared to r1)
delay
mrs.r2.del <- MRsurvival(time.ref="t", status.ref="cens", cov.rel=c("age", "delay"),
            data.rel=r2, cox.ref=cox.r1, cov.ref=c("age", "male"), init=c(0,0), B=50)

# mean and 95% confidence intervals
apply(mrs.r2.del$matrix.coef, FUN="mean", MARGIN=2)
# age    0.633 *
# delay  0.327 .

cbind(mrs.r2.del$lower95.coef, mrs.r2.del$upper95.coef)
#       -95%    +95%
# age    0.268   0.953 *
# delay  0.000   0.617 .
```

CONTINUES IN FIG. 6C

CONTINUES FROM FIG. 6C

.
.

```
# cbt participation adequacy
mrs.r2.cbt <- MRsurvival(time.ref="t", status.ref="cens", cov.rel=c("age", "cbt"),
            data.rel=r2, cox.ref=cox.r1, cov.ref=c("age", "male"), init=c(0,0), B=50)

# mean and 95% confidence intervals
apply(mrs.r2.cbt$matrix.coef, FUN="mean", MARGIN=2)
# age    0.635 *
cbt   -1.576 * cbind(mrs.r2.cbt$lower95.coef, mrs.r2.cbt$upper95.coef)
-95%     +95%
# age    0.357    0.980 *
cbt   -1.904   -1.255 * time to relapse1
mrs.r2.tr1 <- MRsurvival(time.ref="t", status.ref="cens", cov.rel=c("age", "tr1"),
            data.rel=r2, cox.ref=cox.r1, cov.ref=c("age", "male"), init=c(0,0), B=50)

# mean and 95% confidence intervals
apply(mrs.r2.tr1$matrix.coef, FUN="mean", MARGIN=2)
# age    0.390 *
tr1   -0.004 * cbind(mrs.r2.tr1$lower95.coef, mrs.r2.tr1$upper95.coef)
-95%     +95%
# age    0.028    0.670
tr1   -0.004   -0.003 conclude: age has increased relative significance from first intervention to relapse from
second intervention; older age increases hazard rate gender is not significant in this cohort
# in relapse from either first intervention or second intervention delay > 3 mo before re-
# intervention confers slight incremental risk adequate cbt participation strongly decreases
# hazard rate after second intervention (prolongs time to relapse2) longer time to relapse1
# slightly decreases hazard rate after second intervention (prolongs time to relapse2) after
# first relapse, particularly if time to r1 was less than 180 days, intervene early and intensify
# cbt engagement and second intervention outcome will be more durable
```

*FIG. 6C.*

PREDICTING ADDICTION RELAPSE AND DECISION SUPPORT TOOL

CROSS-REFERENCE TO RELATED APPLICATION

This application is a continuation of U.S. patent application Ser. No. 15/719,151, filed Sep. 28, 2017, entitiled "Predicting Addition Relapse and Decision Support Tool", which claims priority to U.S. Provisional Patent Application No. 62/401,160, filed Sep. 28, 2016, entitled "Predicting Addiction Relapse." The aforementioned applications are hereby incorporated by reference herein.

BACKGROUND

Addiction is a primary, chronic disease of brain reward, motivation, memory, and related phenomena. Abnormality in these functions leads to characteristic biological, psychological, social, and spiritual manifestations. This is reflected in an individual pathologically pursuing reward and/or relief by substance use and other behaviors. Addiction is characterized by inability to consistently abstain, impairment in behavioral control, craving, diminished recognition of significant problems with one's behaviors and interpersonal relationships, and a dysfunctional emotional response. Like other chronic diseases, addiction often involves cycles of relapse and remission. Without treatment or engagement in recovery activities, addiction is progressive and can result in disability or premature death.

SUMMARY

This summary is provided to introduce a selection of concepts in a simplified form that are further described below in the detailed description. This summary is not intended to identify key features or essential features of the claimed subject matter, nor is it intended to be used in isolation as an aid in determining the scope of the claimed subject matter.

Embodiments described in this disclosure are directed towards systems and methods for determining an individual's likelihood of relapsing into prior behavior subsequent to a treatment for a mental health or addiction disorder, and in some instances further predicting a likelihood time frame for such a relapse. In particular, embodiments provide for the automatic identification of target subjects having a risk of relapse, non-adherence, or absconding. Some embodiments provide a leading indicator of near-term future abnormalities, proactively notifying supervisory personnel responsible for the person and providing such personnel with timely notice to enable effective corrective, preventive, or trend-modifying maneuvers to be undertaken.

Accordingly, as will be further described herein, one embodiment comprises a method for developing a relapse-risk predictive model, and method for implementing the developed model to identify risk for relapse over a future time interval. The model development begins with identifying a cohort of historical subjects in an electronic health records system with known relapse statuses, and retrieving for the cohort historical values for treatment events, medication history, substance use history, demographic attributes, laboratory tests, or other features that are germane to treatment efficacy. The distributions of ratio-scale and/or interval-scale variables (real-valued variables; count variables; etc.) may be symmetrized and de-skewed by applying suitable transformations such as power-law or logarithmic transforms, and the ratio-scale and/or interval-scale variables may be standardized, so that the arithmetic mean of each is zero and the standard deviation of each is equal to one. Next, dimensionality reduction is performed using Least Absolute Shrinkage and Selection Operator (LASSO) regression with either an L1 absolute-value penalty function or an L2 quadratic ridge penalty function, retaining statistically-significant independent variables for use in subsequent model-generating regression steps. Relative survival regression of the dependent variable on the independent variables retained in the previous step is then performed, via either multiplicative Cox Proportional Hazards relative survival regression or Random Forest relative survival regression. Finally, the developed model, and in particular, the independent variables' regression coefficients, is stored for use in the runtime scenario.

In an embodiment for implementing the developed model, a target subject such as a person potentially at risk for relapse, is identified and a corresponding health record from an electronic health records (EHR) system is accessed. Historical values for the independent variables of the model are extracted from the health record, and if necessary de-skewing and/or standardizing transformations on ratio-scale and interval-scale variables are performed. Next, the model is used to determine a prediction for the target subject's risk for relapse over a future time frame. The prediction may be provided to appropriate caregivers associated with the subject and/or used for scheduling an intervention or otherwise modifying a care for the subject, such as increasing monitoring, pharmaceutical combinations, or reaching out to the subject, for example. In some embodiments, the prediction may be stored and compared against future predictions to determine whether a patient's risk has changed.

Yet another aspect described herein provides for determining relapse risk and time-to-relapse. Such an aspect may begin with receiving, by a data communication controller, information for a target subject. Information may include one or more of the individual's number of prior treatments, attendance at prescribed treatment sessions, participation in prescribed online treatment cognitive behavioral therapy (CBT), first-rank relapse status and time of relapse subsequent to initiation of treatment, age, gender, genotype, mental disorders, mental attributes (such as neuroticism, orderliness, persistence, anxiety index, depression index, interpersonal sensitivity, etc.), psychiatric medications, medications targeting substance cravings, consumption of substance during peak periods, duration of addictive behavior, employment status, financial problems or vagrancy, marital status, social problems or incarceration, treatment withdrawal, duration of abstinence, spirituality, abstinence self-efficacy, multiple addictions, drug metabolism, drug efficacy, and drug negative adverse reactions. In some embodiments the information is categorically graded. In a particular embodiment the time series of attendance information from the target subject is analyzed, by an analyzer, to produce an analysis result. Based on the analysis result a possibility of relapse or non-adherence or absconding and the time-to-relapse or non-adherence for the probationer is calculated. In some embodiments, if a short time-to-relapse or a high possibility of relapse is determined, an alert is sent to a case manager assigned to the subject, thus facilitating immediate intervention prior to actual relapse. In some embodiments, if the possibility of relapse or non-adherence or absconding does not indicate high possibility the possibility of relapse with any past analysis result is compared. In such an embodiment, if a discrepancy between the possibility of relapse and a past analysis result is calculated by the analyzer, an alert is sent to the case manager. In some embodiments the alert indicates to the case manager whether the analyzer determined that the target's potential for relapse was improving (i.e. relapse less probable) or if the target's potential for relapse was worsening (i.e. relapse more probable). In a particular embodiment, if no discrepancy between the possibility of relapse and past analysis results is discovered by the analyzer a notification may be sent to the case manager indicating that the targets status is unchanged. In some embodiments, the alert and/or notification may also be coupled with the automated performance of an action. In particular embodiments, the action may include at least one of placing a new order in the target's EHR; altering the targets care plan; reserving a resource, for the target, in a care facility for treating the particular relapse at issue for the subject; modifying a plan of care for the target; automatically scheduling increased monitoring of the target; ordering increased testing of the target; automatically scheduling a consultation with a specialist care provider/case manager/psychologist/psychiatrist; automatically issuing a clinical order for the patient, including pharmacologic intervention; and issuing an electronic alert or notification to the responsible care provider or patient. In some embodiments the pharmacologic intervention may be the medications targeting substance cravings such as, naltrexone or other mu-opioid receptor antagonists, acamporosate, calcium carbimide, suvorexant or other orexin receptor antagonists, or prazosin or other alpha-1 receptor antagonists.

In a particular aspect, the cohort of historical subjects in an electronic health records system is selected, such that the treatments and relapse statuses and other variables are already known. In some aspects, the subjects' historical values for treatment events, medication history, substance use history, demographic attributes, laboratory tests, or other features that are germane to treatment efficacy are retrieved.

In some aspects, the distributions of ratio-scale and interval-scale variables (real-valued variables; count variables; etc.) may be symmetrized and de-skewed by applying suitable transformations such as power-law or logarithmic transforms as are known to those practiced in the art. In some aspects, the ratio-scale and interval-scale variables may be standardized so that the arithmetic mean of each is zero and the standard deviation of each is equal to one. In some aspects, dimensionality reduction may be performed via Least Absolute Shrinkage and Selection Operator (LASSO) regression with either an L1 absolute-value penalty function or an L2 quadratic ridge penalty function, retaining statistically-significant independent variables for use in subsequent model-generating regression steps. In some aspects, the relative survival regression of the dependent variable on the independent variables retained in the previous step is performed on a second-rank relapse group relative to a first-rank initial relapse group, via either multiplicative Cox Proportional Hazards relative survival regression or Random Forest relative survival regression. In some aspects, the independent variables' regression coefficients may be stored for later use in the run time version of model. In some aspects, the values of model variables that are associated with an individual subject who is to be the target of a prediction are ascertained. In some aspects, the target individual's variables' values are combined mathematically via the model and the model's coefficients to produce a predicted relapse risk for the second-rank or subsequent treatments and/or a predicted time-to-relapse. In some aspects, the predicted second-rank relapse risk and time-to-relapse of the target individual are stored on machine-readable storage media. In some aspects, the predicted relapse risk and time-to-relapse of the target individual are communicated via an alert message or via an electronic health records system to the case manager or probation officer or clinicians who are responsible for the care and supervision of the target individual.

In some aspects, the first-rank events are first occurrences of relapse or non-adherence and second-rank events are the adjacent subsequent (second) occurrences. In some aspects, the first-rank events are first occurrences of relapse or non-adherence and second-rank events are occurrences of some other subsequent but non-adjacent ordinal occurrences (e.g., 'fourth relapse'). In some aspects, the first-rank events are first occurrences of relapse or non-adherence and second-rank events are all subsequent occurrences (e.g., 'third through N-th relapse'). In some aspects, the first-rank events are members of a grouping of "early" occurrences of relapse of non-adherence where 'early' is defined by context-dependent attributes and second-rank occurrences are members of a grouping of subsequent "late" occurrences, where the 'late' grouping is likewise defined by context-dependent attributes denoting lateness. In some aspects, the statistically significant independent variables and pairwise variable-variable interactions are first identified by means of Random Forest or variable importance (VIMP) methods, prior to performing Relative Survival Modeling.

In this way, embodiments provide for use in general care venues and afford a degree of robustness against transient or intermittent non-appearances that are low-risk, and against variations in individual conditions and logistical factors that relate to the individual's ability to adhere to the prescribed program. Further, embodiments facilitate subject tracking, monitoring, and/or warning and learning and reinforcing systems and methods that permit prediction of relapse of a subject who is under treatment for an addiction disorder.

BRIEF DESCRIPTION OF THE DRAWINGS

The present invention is described in detail below with reference to the attached drawing figures, wherein:

FIG. 3A-3D depict aspects of an example embodiment actually reduced to practice for predicting risk for alcohol dependency and relapse, including a receiver operating characteristic (ROC) curve and statistical performance of the example embodiment;

FIGS. 4A and 4B Kaplan-Meier survival curves for time to relapse 1 and time to relapse 2 events, in accordance with an embodiment of the disclosure;

FIG. 5 depicts an example clinician user interface for use in predicting a subject's risk for relapse over a future time interval, in accordance with an embodiment of the disclosure; and FIGS. 6A-6C illustratively depict an example embodiment of a computer program routine for determining predictors of relapse or non-adherence in an individual (i.e., predictive model development time) and for predicting relapse or non-adherence in an individual (i.e., predictive model run time).

DETAILED DESCRIPTION

Figure 1A:
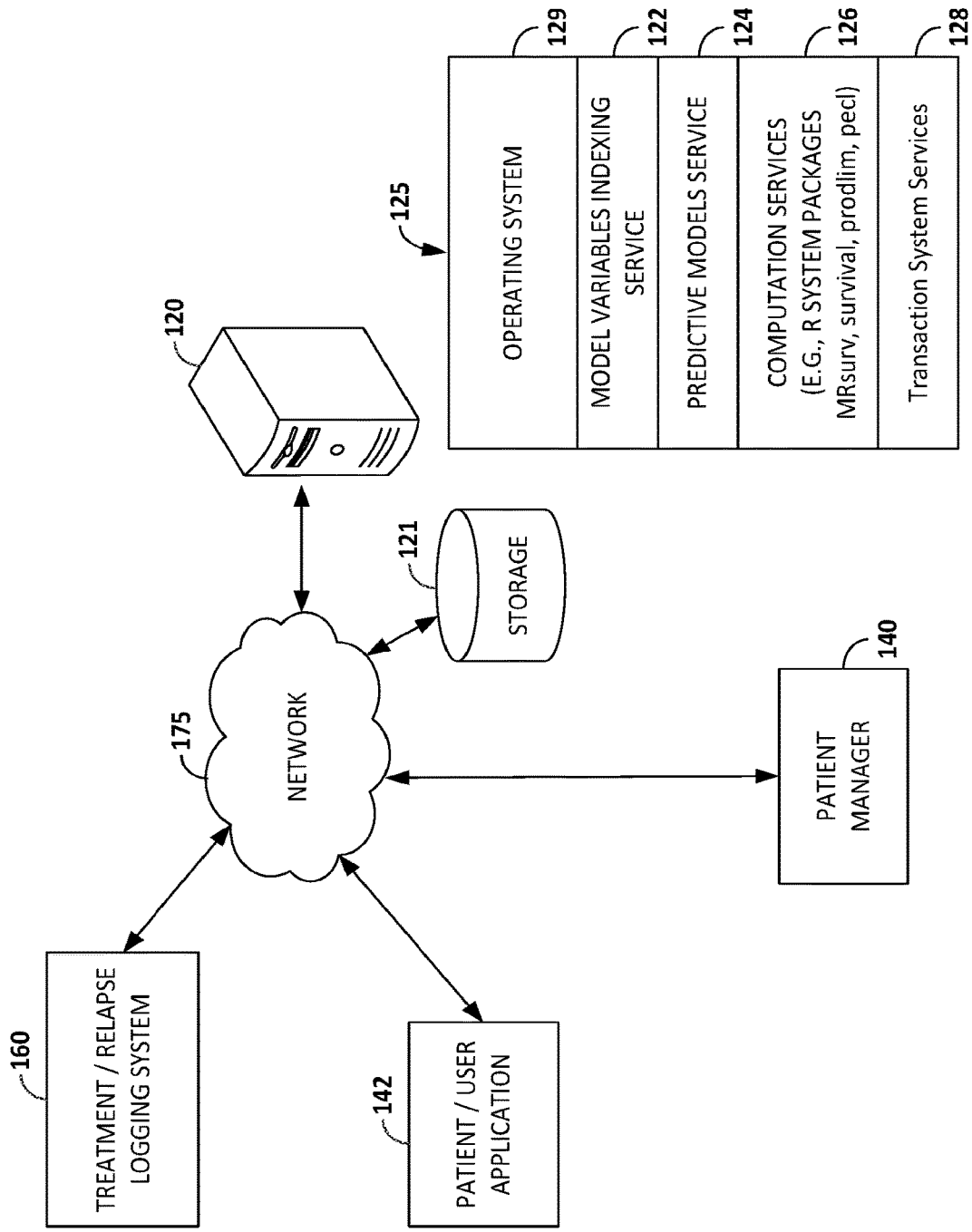
FIGS. 1A and 1B depict aspects of an illustrative operating environment suitable for practicing an embodiment of the disclosure.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of our invention may be embodied as, among other things: a method, system, or set of instructions embodied on one or more computer readable media. Accordingly, the embodiments may take the form of a hardware embodiment, a software embodiment, or an embodiment combining software and hardware. In one embodiment, the invention takes the form of a computer-program product that includes computer-usable instructions embodied on one or more computer readable media.

Computer-readable media can be any available media that can be accessed by a computing device and includes both volatile and nonvolatile media, removable and non-removable media. By way of example, and not limitation, computer-readable media comprises media implemented in any method or technology for storing information, including computer-storage media and communications media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing device 100. Computer storage media does not comprise signals per se. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

As described above, system, methods, and computer-readable media are provided herein for the automatic identification of target subjects having a risk of relapse, non-adherence, or absconding. Thus, an aim of some embodiments relates to automatically identifying persons who are at risk for relapse in addiction behavior. In particular, some embodiments provide for patient/subject tracking, monitoring, warning and/or learning and reinforcing systems and methods that permit prediction of relapse of a subject who is under treatment for an addiction disorder.

The long-lasting, chronic nature of many addictions and high rates of relapse present a considerable challenge for the treatment of drug and alcohol addiction, such that understanding of the predictors of relapse has emerged as a central issue in addiction research and treatment. Emotional and environmental factors (conditioning stimuli) are among the main antecedents of relapse. For example, it is known that specific stress conditions such as loss of work and economic difficulties, or stimuli predictive of the presence of alcohol previously associated with its use such as a bottle of the subject's preferred wine and a bar-like environment may strongly facilitate relapse in previously rehabilitated alcoholics.

Homeostatic hypotheses relate relapse risk to neuroadaptive changes and disruption of neuroendocrine homeostasis that are thought to underlie anxiety, disordered sleep patterns, mood dysregulation and somatic symptoms that accompany acute withdrawal, and that can persist for considerable periods of time during what has been referred to as the "protracted withdrawal" phase. This view implicates alleviation of discomfort and negative affect as a motivational basis for relapse.

Conditioning hypotheses are based on observations that relapse is often associated with exposure to substance-related environmental stimuli. This view holds that specific environmental stimuli that have become associated with the rewarding actions of a drug by means of classical conditioning can elicit psychosocial states that trigger resumption of substance use. The homeostatic and conditioning components are not mutually exclusive. In fact, homeostatic and conditioning factors are likely to exert combined effects in that exposure to substance-related environmental stimuli may augment vulnerability to relapse conveyed by homeostatic disturbances.

Substance use disorders are common, but only a small minority of patients receive adequate treatment. It is well known that a large proportion of patients with addiction relapse after treatment. In a controlled setting, such as inpatient or residential treatment, most patients can abstain from drugs, but after discharge, many patients quickly begin drinking or using drugs again. Although psychosocial therapies, including 12-step programs, are reasonably effective, relapse is common. In North America, approximately 90% of people recovering from substance addiction will relapse within 48 months after treatment. Thus, there is a need in the art for new and improved systems methods for treating and preventing addiction and the relapse use of addictive agents. Accordingly, some embodiments described herein meet these needs by providing methods and/or pharmaceutical combinations useful in treating and preventing addiction and relapse.

Some of the systems and methods described herein address personalized prediction of relapse for patients with alcohol, opioid, or cocaine use disorders. Disulfiram, acamprosate, and the opioid antagonist naltrexone have for many years been used for the treatment of alcoholism. Recently, one novel approach is the use of the mu-opioid antagonist and partial kappa-opioid agonist nalmefene to reduce alcohol consumption. Other novel pharmacological approaches include the GABA-B receptor agonist baclofen, anticonvulsants such as topiramate and gabapentin, the partial nicotine receptor agonist varenicline, and other drugs, such as suvexorant, an orexin antagonist that normalizes disordered sleep patterns in many individuals. For opioid dependence, opioid agonist therapy with methadone or buprenorphine is the first-line treatment option. Other options include oral or depot naltrexone, morphine sulfate, depot or implant formulations, and heroin (diacetylmorphine) in treatment-refractory patients. To date, no pharmacological treatment has been approved for cocaine addiction; however, three potential pharmacological treatments have been studied: disulfiram, methylphenidate, and modafinil. Pharmacogenetic and genomics approaches may help to optimize treatment response in otherwise treatment-refractory patients and to identify which patients are more likely to respond to treatment. Neuromodulation techniques such as repeated transcranial magnetic stimulation (TMS) and deep brain stimulation (DBS) also may play a role in the treatment of substance use disorders. Although no universally efficacious treatment is in sight for treatment-refractory patients, some novel medications and brain stimulation techniques have the potential to improve treatment efficacy for some patients.

To prevent relapse, treatment providers may offer aftercare, e.g., in the form of cognitive behavioral therapy (CBT) or psychotherapy or counselling, or case management. However, to make the best of limited resources, it is important to identify patients with an especially high risk of relapse and an especially high need for aftercare services. If patients who are likely to need aftercare services can be identified early in treatment, caseworkers can focus their efforts to plan for aftercare for these patients.

For example, a number of studies have identified predictors of alcohol relapse after discharge from an alcohol treatment program. These variables include biological markers, personality features, psychiatric disorders, social characteristics, patterns of substance use and misuse, such as length of drinking history and age of onset, and other treatment variables. However, in many instances the practical utility of known predictors of relapse depends primarily on whether the predictors are assessed in treatment settings in a way that allows identification of patients at high risk of relapse or short time-to-relapse, and subsequently undertake interventions that address the increased relative hazard.

Conventional approaches to this problem do not adequately predict or account for relative hazard in patients receiving treatment after relapse subsequent to initial treatment. For example, conventional approaches generally fail to account for situationally created perceptions of a hazard as compared to legitimate hazards for relapse. Generally speaking, the failure of these conventional approaches is rooted, at least in part, in the technological limitations inherent in conventional predictive medicine. Therefore, there is a need for a monitoring, prediction, and management system and method that are based on a treatment rank-ordered relative-hazard "relapse prevention model" which enables case managers to better individualize the plan of care of patients after the first relapse, such as provided herein. In particular, some embodiments enable timely identification of those who are at high risk of relapse or non-adherence in second-rank treatment. Further, in one predictive embodiment, a prediction for time-to-relapse is determined in a subset of persons in who intensified monitoring or alternative interventions may be needed.

Referring now to the drawings in general, and initially to FIG. 1A in particular, an aspect of an operating environment 100 is provided suitable for practicing an embodiment of the technologies described herein. We show certain items in block-diagram form more for being able to reference something consistent with the nature of a patent specification than to imply that a certain component is or is not part of a certain device. Similarly, although some items are depicted in the singular form, plural items are contemplated as well (e.g., what is shown as one data store might really be multiple data-stores distributed across multiple locations). But showing every variation of each item might obscure the invention. Thus for readability, we show and reference items in the singular (while fully contemplating, where applicable, the plural).

As shown in FIG. 1, example operating environment 100 provides an aspect of a computerized system for compiling and/or running aspects of this disclosure, which in some embodiments may include collecting and analyzing unstructured text data from electronic health record(s), which may include claims data, to assess the texts as to topical or concept-oriented expressions they contain that are statistically similar to those associated with various clinical conditions or diagnoses; to identify which condition- or diagnosis-oriented clusters the present texts most closely resemble, if any; and to notify the responsible clinicians of those determinations, suggesting consideration of those conditions or diagnoses as part of the constellation of differential diagnoses pertinent to the management of the current patient.

Operating environment 100 is one example of a suitable environment and system architecture for implementing an embodiment of the disclosure. As described above, some embodiments may be implemented as a system, comprising one or more computers and associated network and equipment, upon which a method or computer software application is executed. Accordingly, aspects of the present disclosure may take the form of an embodiment combining software and hardware aspects that may all generally be referred to herein as a "module" or "system." Further, the methods of the present disclosure may take the form of a computer application embodied in computer readable media having machine-readable application software embodied thereon. In this regard, a machine-readable storage media may be any tangible medium that can contain, or store a software application for use by the computing apparatus.

Computer application software for carrying out operations for steps of the methods of the present disclosure may be authored in any combination of one or more programming languages, including an object-oriented programming language such as Java, Python, R, or C++ or the like. Alternatively, the application software may be authored in any or a combination of traditional non-object-oriented languages such as C or Fortran. The application may execute entirely on the user's computer as an independent software package, or partly on the user's computer in concert with other connected co-located computers or servers, or partly on the user's computer and partly on one or more remote computers, or entirely on a remote computer or collection of computers. In the latter cases, the remote computers may be connected to the user's computer through any type of network, including a local area network (LAN) or a wide area network (WAN), or the connection may be made to an external computer (for example, via the internet using an Internet Service Provider or ISP) or an arbitrary, geographically-distributed, federated system of computers, such as a cloud-based system.

Environment 100 includes a treatment/relapse logging system 160, which may be part of one or more electronic health record (EHR) systems, communicatively coupled to network 175, which is communicatively coupled to computer system 120. In some embodiments, components of environment 100 that are shown as distinct components may be embodied as part of or within other components of environment 100. For example, treatment/relapse logging system systems 160 may comprise one or a plurality of record/logging systems such as hospital EHR systems, health information exchange EHR systems, clinical genetics/genomics systems, ambulatory clinic EHR systems, psychiatry/neurology EHR systems, insurance, collections or claims records systems; and may be implemented in computer system 120. In an embodiment, treatment/relapse logging system 160 includes historical data for patient addition treatment, relapse information, other health services, claims data, apportionment data, and/or related health services financial data.

In some embodiments, sequence itemset mining is performed using data about a population of patients derived from patient EHR information. In particular, presently certain data warehouses are created for purposes of public health and observational research purposes and are derived from electronic health records repositories in such a way that they are de-identified so as to comply with applicable confidentiality laws and regulations. The Cerner Health Facts™ data warehouse is such a system that has been curated for more than 15 years. It comprises a large 'transaction database' where each entry corresponds to a patient's 'basket' (a collection of items recorded or transacted at points in time during episodes of care services provisioning in the contributing health care institutions). Each database entry is ordered by the date-time of the transaction. Transaction sequencing is implemented by grouping medical events occurring in the same 'epoch' for the same patient together into 'baskets' and ordering the 'baskets' of each patient by the date-time stamps where the events occurred. Epoch durations may differ according to the age of the patient, or the acute or chronic nature of the health conditions that pertain to the patient, or the rate of change of the severity of the health conditions, or other factors, Epoch durations may be as short as a few minutes (as in critical care ICU or operating room contexts) or may be as long as 10 years or more (as in chronic ambulatory care-sensitive conditions, ACSCs).

Continuing with FIG. 1A, network 175 may comprise the Internet, and/or one or more public networks, private networks, other communications networks such as a cellular network, or similar network(s) for facilitating communication among devices connected through the network. In some embodiments, network 175 may be determined based on factors such as the source and destination of the information communicated over network 175, the path between the source and destination, or the nature of the information. For example, intra-organization or internal communication may use a private network or virtual private network (VPN). Moreover, in some embodiments items shown communicatively coupled to network 175 may be directly communicatively coupled to other items shown communicatively coupled to network 175.

In some embodiments, operating environment 100 may include a firewall (not shown) between a first component and network 175. In such embodiments, the firewall may reside on a second component located between the first component and network 175, such as on a server (not shown), or reside on another component within network 175, or may reside on or as part of the first component.

Embodiments of treatment/relapse logging system 160 may comprise one or more data stores of health records, which may be stored on storage 121, and may further include one or more computers or servers that facilitate the storing and retrieval of the health records. In some embodiments, treatment/relapse logging system 160 may be implemented as a cloud-based platform or may be distributed across multiple physical locations. Treatment/relapse logging system 160 may further include record systems, which store real-time or near real-time patient (or user) information, such as wearable, bedside, or in-home patient monitors or sensors, for example. Although FIG. 1A depicts an exemplary treatment/relapse logging system 160, it is contemplated that an embodiment relies on patient manager 140 and/or patient/user application 142 for accessing, storing and/or retrieving patient record information.

Example operating environment 100 further includes a patient/user application 142 communicatively coupled through network 175 to treatment/relapse logging system 160. Although environment 100 depicts an indirect communicative coupling between application 142 and treatment/relapse logging system 160 through network 175, it is contemplated that an embodiment of application 142 is communicatively coupled to treatment/relapse logging system 160 directly. An embodiment of application 142 comprises a software application or set of applications residing on a client computing device (or distributed in the cloud and on a client computing device) such as a personal computer, laptop, smartphone, tablet, or mobile computing device. In an embodiment, the application is a smartphone app, a Web-based application or an applet, and may be used to provide or manage user services provided by an embodiment of the disclosure, which may be used by the target user at risk for relapse, a social worker, or caregiver associated with the target user. For example, in one embodiment, application 142 facilitates receiving and logging treatment-related (or relapse related) information about the target user and/or processing, interpreting, accessing, storing, retrieving, and communicating information associated with treatment logged records or other healthcare related records of the target user. In an embodiment, application 142 sends an alarm indication directly to patient manager 140 through network 175.

Example operating environment 100 also includes a patient manager 140 communicatively coupled through network 175 to treatment/relapse logging system 160 and patient/user application 142. In one embodiment of manager 140 comprises a user interface that may be used to facilitate access by a user (including a clinician/caregiver such as a medical or psychiatric caregiver) to the target user's health records (including information logged in component 160), and one or more prediction models for predicting likelihood of relapse of the target user. One embodiment of patient manager 140 takes the form of a user interface and application, which may be embodied as a software application operating on one or more mobile computing devices, tablets, smartphones, front-end terminals in communication with back-end computing systems, laptops, or other computing devices. In an embodiment, the application includes the PowerChart® software manufactured by Cerner Corporation. In an embodiment, manager 140 includes a Web-based application (which may take the form of an applet or app) or set of applications usable to manage user services provided by an embodiment of the invention.

In some embodiments, manager 140 facilitates accessing and receiving information from a user or health care provider about a specific patient, set of patients, or provider clinicians, according to the embodiments presented herein. Embodiments of manager 140 also may facilitate accessing and receiving information from a user or health care provider about a specific patient or population of patients including patient history; health care resource data; variables measurements, timeseries, and predictions (including plotting or displaying the determined outcome and/or issuing an alert) described herein; or other health-related information, and facilitates the display of results, recommendations, or orders, for example. In an embodiment, manager 140 also facilitates receiving orders for the patient/target user from the clinician/caregiver, based on the results of monitoring and/or predictions. Manager 140 may also be used for providing diagnostic services or evaluation of the performance of various embodiments. An example of an aspect of a user interface for use via manager 140 is illustratively provided in FIG. 5.

Example operating environment 100 further includes computer system 120, which may take the form of a server, which is communicatively coupled through network 175 to EHR system 160, and storage 121.

Computer system 120 comprises one or more processors operable to receive instructions and process them accordingly, and may be embodied as a single computing device or multiple computing devices communicatively coupled to each other. In one embodiment, processing actions performed by system 120 are distributed among multiple locations such as one or more local clients and one or more remote servers, and may be distributed across the other components of example operating environment 100. For example, a portion of computing system 120 may be embodied on application 142. In one embodiment, system 120 comprises one or more computing devices, such as a server, desktop computer, laptop, or tablet, cloud-computing device or distributed computing architecture, a portable computing device such as a laptop, tablet, ultra-mobile P.C., or a mobile phone.

Embodiments of computer system 120 include computer software stack 125, which in some embodiments operates in the cloud, as a distributed system on a virtualization layer within computer system 120, and includes operating system 129. Operating system 129 may be implemented as a platform in the cloud, and which is capable of hosting a number of services such as 122, 124, 126, and 128. Some embodiments of operating system 129 comprise a distributed adaptive agent operating system. Embodiments of services 122, 124, 126, and 128 run as a local or distributed stack in the cloud, on one or more personal computers or servers such as system 120, and/or a computing device running interfaces 140 and 142. In some embodiments, application 142 and/or manager 140 operate in conjunction with software stack 125.

In embodiments, model variables indexing (or mapping) service 122 facilitate retrieving frequent item sets, extracting database records, and cleaning the values of variables in records. For example, service 122 may perform functions for synonymic discovery, indexing or mapping variables in records, or mapping disparate health systems' ontologies, such as determining that a particular medication frequency of a first record system is the same as another record system. In some embodiments, these services may invoke computation services 126. Predictive models service 124 comprises the services or routines for forecasting likelihood of patient relapse, which may be developed according to the method described in connection to FIG. 2A and implemented in accordance with the method described in connection to FIG. 2B.

Computation services 126 perform statistical software operations, and include statistical calculation packages such as, in one embodiment, the R system (the R-project for Statistical Computing, which supports R-packages or modules tailored for specific statistical operations, and which is accessible through the Comprehensive R Archive Network (CRAN) at http://cran.r-project.org) or similar services, and R-system modules or packages including, in an embodiment, MRsury or survival packages, which may be utilized during model development for multiplicative-regression models for relative survival, and prodlim package for performing product-limit estimation for censored event history analysis, used in the implementation of the predictive model (s) for determining likelihood of relapse. Some embodiments of computational services 126 may include the R-system package pecl.

In some embodiments, computational services include natural language processing services (not shown) such as Discern nCode™ developed by Cerner Corporation, or similar services. In an embodiment, computation services 126 include the services or routines, which may be embodied as one or more software agents or routines such as the example embodiments of computer program routines illustratively provided in FIGS. 6A-6C. In some embodiments, computation services 126 use treatment/relapse logging system 160. Some embodiments of computation services 126 may use transaction systems services 128. Transaction system services 128 include services for facilitating transactions by a target user, which may be facilitated using application 142, and/or by a clinician, caregiver, or provider, which may be facilitated using patient manager 140.

Some embodiments of stack 125 may further use Apache Hadoop and Hbase framework (not shown), or similar frameworks operable for providing a distributed file system, and which in some embodiments facilitate provide access to cloud-based services such as those provided by Cerner Healthe Intent®. Additionally, some embodiments of stack 125 may further comprise one or more services stream processing service(s) (not shown). For example, such stream processing service(s) may be embodied using IBM InfoSphere stream processing platform, Twitter Storm stream processing, Ptolemy or Kepler stream processing software, or similar complex event processing (CEP) platforms, frameworks, or services, which may include the user of multiple such stream processing services (in parallel, serially, or operating independently). Some embodiments of the invention also may be used in conjunction with Cerner Millennium®, Cerner CareAware® (including CareAware iBus®), Cerner CareCompass®, or similar products and services.

Example operating environment 100 also includes storage 121 (or data store 121), which in some embodiments includes patient data for a candidate or target patient (or information for multiple patients), including raw and processed patient data; variables associated with patient recommendations; recommendation knowledge base; recommendation rules; recommendations; recommendation update statistics; an operational data store, which stores events, frequent itemsets (such as "X often happens with Y", for example), and item sets index information; association rulebases; agent libraries, solvers and solver libraries, and other similar information including data and computer-usable instructions; patient-derived data; and health care provider information, for example. It is contemplated that the term data includes any information that can be stored in a computer-storage device or system, such as user-derived data, computer usable instructions, software applications, or other information. In some embodiments, data store 121 comprises the data store(s) associated with treatment/relapse logging system 160. Further, although depicted as a single storage data store, data store 121 may comprise one or more data stores, or may be in the cloud.

Figure 1B:
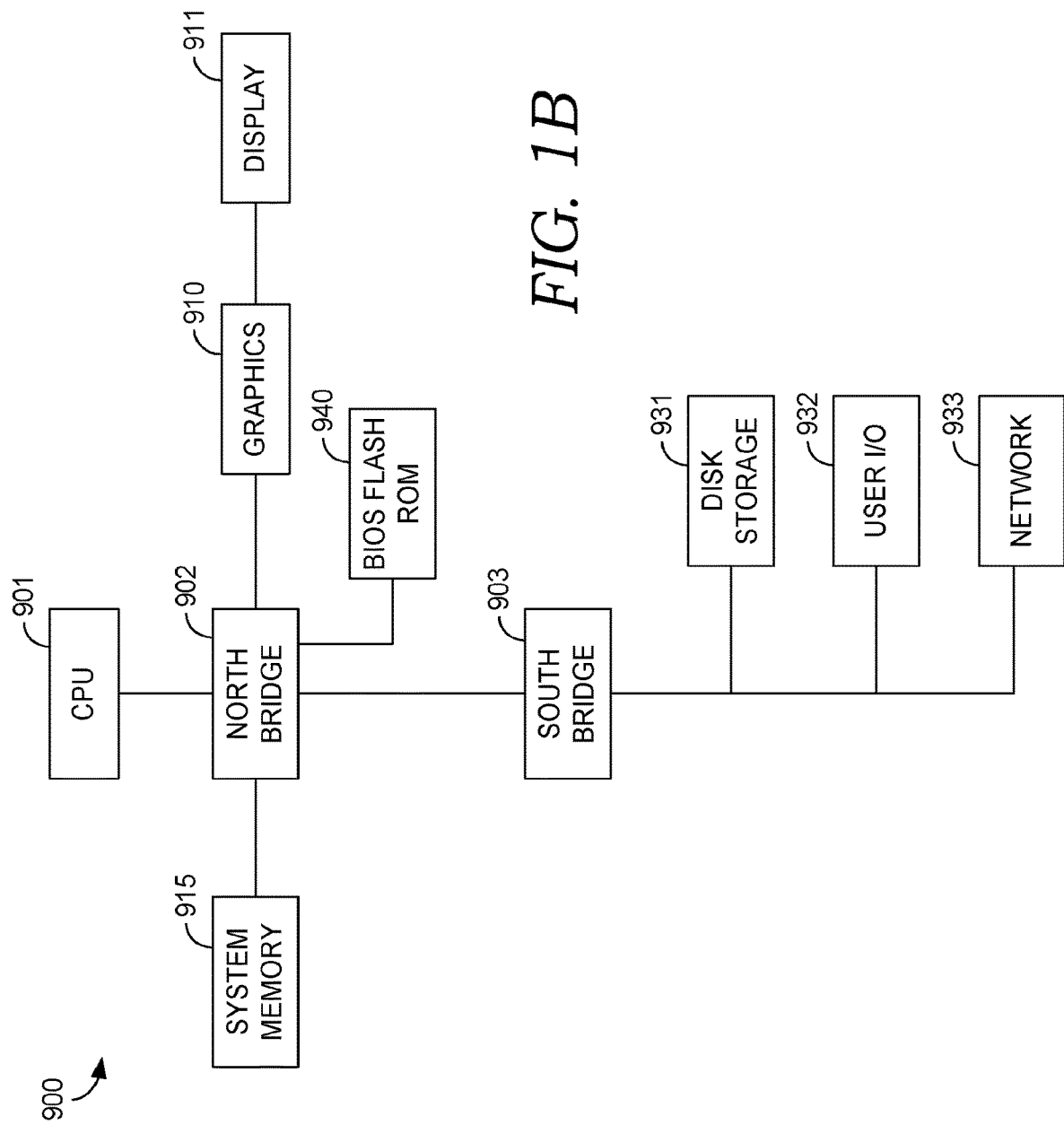

Turning briefly now to FIG. 1B, there is shown one example embodiment of computing system 900 that has software instructions for storage of data and programs in computer-readable media. Computing system 900 is representative of a system architecture that is suitable for computer systems such as computing system 120. One or more CPUs such as 901, have internal memory for storage and couple to the north bridge device 902, allowing CPU 901 to store instructions and data elements in system memory 915, or memory associated with graphics card 910, which is coupled to display 911. Bios flash ROM 940 couples to north bridge device 902. South bridge device 903 connects to north Bridge device 902 allowing CPU 901 to store instructions and data elements in disk storage 931 such as a fixed disk or USB disk, or to make use of network 933 for remote storage. User I/O device 932 such as a communication device, a mouse, a touch screen, a joystick, a touch stick, a trackball, or keyboard, couples to CPU 901 through south bridge 903 as well. The system architecture depicted in FIG. 1B is provided as one example of any number of suitable computer architectures, such as computing architectures that support local, distributed, or cloud-based software platforms, and are suitable for supporting computing system 120.

Returning to FIG. 1A, in some embodiments, computer system 120 is a computing system made up of one or more computing devices. In some embodiments, computer system 120 includes one or more software agents, and in an embodiment includes an adaptive multi-agent operating system, but it will be appreciated that computer system 120 may also take the form of an adaptive single agent system or a non-agent system. Computer system 120 may be a distributed computing system, a data processing system, a centralized computing system, a single computer such as a desktop or laptop computer or a networked computing system.

Figures 2A, 2B:
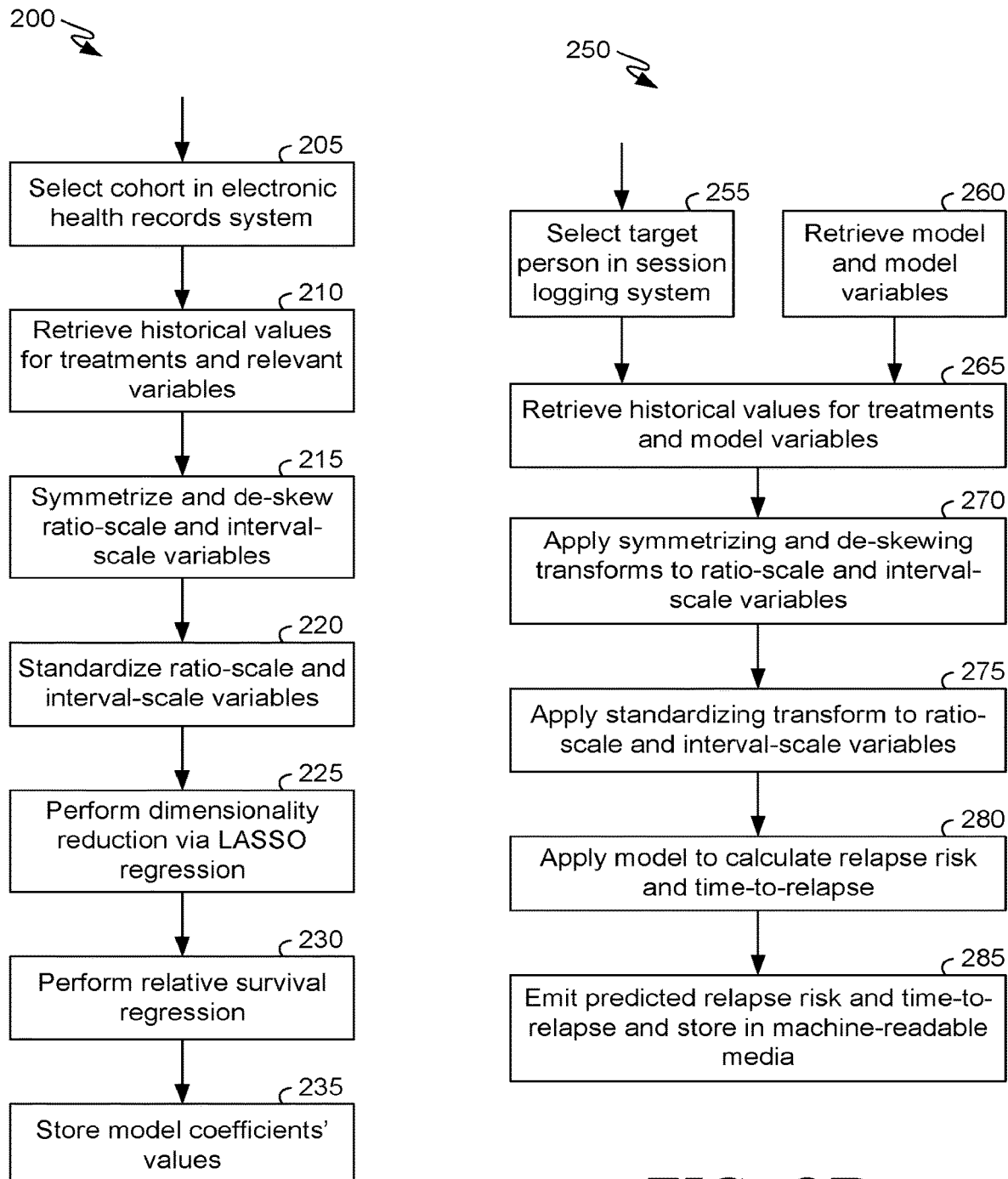
FIGS. 2A and 2B depicts flow diagrams of a method for determining predictors of relapse or non-adherence in an individual (i.e., predictive model development time), and method for automatically predicting relapse or non-adherence in an individual (i.e., predictive model run time), in accordance with an embodiment of the disclosure.

Turning now to FIGS. 2A and 2B, method 200 is provided for determining predictors of relapse or non-adherence in an individual (i.e., predictive model development time), and a method 250 is provided for automatically predicting relapse or non-adherence in an individual (i.e., predictive model run time). With reference to methods 200 and 300, embodiments are described which may be used for a monitoring, prediction, and management system based on a treatment rank-ordered relative-hazard "relapse prevention model" which thereby enables patient case managers to better individualize the plan of care of patients after the first relapse, such as provided herein.

An excess hazard is determined by subtracting the expected hazard rate from the observed hazard rate (additive hazard model). Whereas excess hazard and relative hazard represent different ways of analyzing the observed hazard rate in the target cohort compared to the background reference population. To date, there are no strong arguments in the research literature for choosing an additive hazard model rather than a multiplicative hazard model. Excess mortality has been widely used in cancer research to estimate mortality in population-based studies. However, relative mortality is more commonly used in chronic conditions.

Conventional comparisons of risk factors between both groups would imply testing all the interactions with the treatment rank, which even when feasible often yields unstable or inaccurate results due to inadequate sample size to power the statistical regression or modeling process. Secondly, second-rank specific explanatory variables (survival time to first relapse, treatment modalities in the first treatment, etc.) cannot be included in relative survival regression analyses despite the knowledge that their use would improve risk evaluation, owing to the fact that values for these are absent in the first-rank comparator population. To overcome these conventional limits, embodiments of this disclosure use an alternative strategy, an adaptation of a multiplicative-regression model for relative survival (MRS). As such, embodiments described herein use unconventional techniques within the field of predictive medical treatment.

Calculation of relative relapse rate is based on a multiplicative hazard model. The observed hazard in a second-rank population [post-relapse] $\lambda_{obs(t)}$ is the product of the expected hazard of a background population (e.g., first-rank treated patients) Ab ac k (t) and a relative hazard $\lambda_{rel}(t)$:

$$\lambda_{obs}(t) = \lambda_{back}(t) * \lambda_{rel}(t)$$

Thus, the multiplicative relative hazard of members of the second-rank population compared to the first-rank comparator population is:

$$\lambda_{rel}(t) = \frac{\lambda_{obs}(t)}{\lambda_{back}(t)}$$

The multiplicative relative hazard rate provides a direct comparison between the observed hazard in the cohort of interest and the hazard in the comparator background population. For example, if the relative hazard in the second-rank cohort is 2.0, then the hazard in this cohort is twice the rate expected in the background population. Multiplicative relative hazard rate can be estimated by the Cox Proportional Hazard regression, by Random Forest relative survival modeling, and by other methods.

Returning to FIGS. 2A and 2B, some embodiments of the steps of methods 200 and 250 may be carried out using one or more computer program routines, such as the routine illustratively provided in FIGS. 6A-6C. Accordingly, method 200 begins at step 205, wherein a cohort of historical subjects in an electronic health records system with known relapse statuses is identified. Known relapse statuses may be determined in a variety of ways. In some embodiments, for example, a treatment/relapse logging system, such as treatment/relapse logging system 160, may identify a plurality of subjects with documented substance use treatment events and/or documented relapse events in the subject's electronic medical record. For example, blood/hair/oral swab tests may indicate THC and/or its metabolites, opioids and/or their metabolites, and so on. In some embodiments, relapse status may be indicated in a health records system by data collected via communicatively coupled at home detection devices; such as commercial and/or analytic grade BAC devices, Bluetooth/WiFi/network enabled wearable technology or medical devices.

The identified subjects may then be compiled into one or more cohorts. In an embodiment, the subjects may be identified by ICD-9 diagnoses with a range indicative of substance use/abuse/treatment/relapse events. As a non-limiting example, a cohort may be identified for relapse of alcohol abuse based on ICD-9 diagnoses in the 303.xx range. However, it will be understood by those skilled in the art, that ICD-9 diagnoses of different ranges can be used to identify cohorts of different abused substances. In an embodiment model variables indexing service 122 may facilitate the treatment/relapse logging system's identification of the plurality of subjects for inclusion in the cohort.

At step 210, historical values for treatment events, medication history, substance use history, demographic attributes, laboratory tests, or other features that are germane to treatment efficacy corresponding to the cohort determined in step 205 are retrieved. In some embodiments of step 210, a treatment/relapse logging system, such as treatment/relapse logging system 160, may capture historical values for treatment events, medication history, substance use history, demographic attributes, laboratory tests associated with each subject included in the cohort. In an embodiment the information may be stored in an EHR system associated with the treatment/relapse logging system and/or a storage system accessible by the treatment/relapse logging system, such as storage 121. For example, a model for alcohol dependency at step 210 may retrieve carbohydrate deficient transferrin results, BAC results provided by a commercial and/or analytic grade instrument. Historical GC/MS results for THC and/or its metabolites for marijuana abuse relapse modeling, or opioids and/or their metabolites for heroin, opium, morphine, and/or other opioid dependency modeling may be retrieved. In some embodiments, a cohort member's historical participation with CBT activities may be retrieved in step 210. For example, historical participation may be determined from the user login information captured by a treatment/relapse logging system 160. For a further example, the system may capture time data while a cohort member interacted with various prompts in an app/internet/computer based CBT activity.

Additionally, relevant information may also include documented indications of possible aberrant behavior. For instance, failure to use a Bluetooth enabled inhaler or a change in the time and/or frequency of device-phone and/or device-health system synchronization events may be relevant information in some embodiments. Additionally, some embodiments may provide biometric authentication procedures for some data sources. For example, iris recognition, figure print detection, retina scan, voice analysis, facial recognition, and/or vascular pattern recognition may be used by a communicatively coupled device to provide biometric authentication for the underlying information. In such a case, the information provided by the data source and/or the coexistence or absence of a biometrically confirmed submission may be relevant. As such, some embodiments of step 265 may access authentication data associated with CBT and/or at home device provided data. In some embodiments, the biometric authentication and the underlying information may be from the same device or different communicatively coupled devices.

It will be understood by those with skill in the art that the previous are intended as illustrative examples and not intended to limit the scope of the embodiments described herein. For example, in some instances, the number of "puffs" detected from a Bluetooth enabled inhaler and/or ER visits coupled with administration of a short-acting beta agonist and/or corticosteroids may be relevant to predictive modeling of noncompliance for asthma patients.

In some embodiments of step 210, treatment/relapse logging system 160 may securely transmit the historical values for treatment events, medication history, substance use history, demographic attributes, laboratory tests associated with each subject included in the cohort, via network 175, to a software stack 125 operating a computation service 126. In some embodiments, step 210 may further comprise de-identifying the subjects included in the cohort. Additionally, some embodiments of step 210 may continue to step 215. However, some embodiments of step 210 may bypass step 215 and/or step 220 and proceed to step 220 or step 225.

At step 215, symmetrized and de-skewed the distributions of ratio-scale and/or interval-scale variables (real-valued variables; count variables; etc.). In an embodiment, step 215 may comprise applying suitable transformations such as power-law or logarithmic transforms. In some embodiments of step 215, computation service 126 may symmetrize and de-skew the distributions of ratio-scale and/or interval-scale variables by applying suitable transformations such as power-law or logarithmic transforms on at least one set of the historical values for treatment events, medication history, substance use history, demographic attributes, and laboratory tests associated with each subject included in the cohort. Additionally, some embodiments of step 215 may continue to step 220. However, some embodiments of step 215 may bypass step 220 and proceed to step 225.

At step 220, the ratio-scale and/or interval-scale variables are standardized. In an embodiment of step 220, the variables are standardized so that the arithmetic mean of each is zero and the standard deviation of each is equal to one. In some embodiments of step 220, computation service 126 may standardize the variables so that the arithmetic mean of each is zero and the standard deviation of each is equal to one.

At step 225, dimensionality reduction is performed using Least Absolute Shrinkage and Selection Operator (LASSO) regression. In an embodiment, LASSO regression is carried out with either an L1 absolute-value penalty function or an L2 quadratic ridge penalty function, retaining statistically-significant independent variables for use in subsequent model-generating regression steps. In some embodiments of step 225, computation service 126 may reduce the dimensionality of the variables using LASSO regression.

At step 230, relative survival regression is performed. In an embodiment, step 230 comprises performing relative survival regression of the dependent variable on the independent variables retained from step 225. In an embodiment, step 230 may utilize either multiplicative Cox Proportional Hazards relative survival regression or Random Forest relative survival regression, and/or may utilize the MRsury or survival R-packages of computational services 126. In some embodiments of step 230, treatment/relapse logging system 160 may receive an indication from the software stack 125, through network 175, that computational services 126 has developed coefficient values for use in the predictive model.

At step 235, the coefficients corresponding to the predictive model develop via method 200 are stored such that the predictive model may be used for predicting risk of relapse for a target user, as described in connection to method 250 of FIG. 2B. Embodiments of step 235 may be facilitated by automated remote commands from treatment/relapse logging system 160. For example, in response to the receiving an indication from the software stack 125 that the computational services 126 has developed the coefficient values for use in the predicative model, treatment/relapse logging system 160 may provide remote commands to software stack 125 to store the coefficients in a data storage system accessible to predicate model service 124.

Turning to FIG. 2B, method 250 begins at step 255, wherein a target subject such as a person potentially at risk for relapse, is identified. The predictive model and model variables, which may be determined according to method 200, in an embodiment, are retrieved at step 260. At step 265, a health record corresponding to the subject identified in step 255 is accessed and historical values for the independent variables of the model are extracted from the health record. For example, if the subject suffers from alcohol dependency, at step 265 may retrieve carbohydrate deficient transferrin results, and/or BAC results provided by a commercial and/or analytic grade instrument. For another example, the subject's GC/MS results for THC and/or its metabolites, or opioids and/or their metabolites may also be retrieved at step 265. In some embodiments, the subject's participation with CBT activities may be retrieved in step 265. For example, participation may be determined from the user login information captured by a treatment/relapse logging system 160 through patient/user application 142. For a further example, the system may capture time data while the subject interacted with various prompts in an app/internet/computer based CBT. However it will be understood by those with skill in the art that the previous examples are illustrative in nature and not intended to limit the scope of the embodiments described herein. For example, relevant information may also include documented indications of aberrant behavior. For instance, failure to use a Bluetooth enabled inhaler or a change in the time and/or frequency of device-phone and/or device-health system synchronization events may be relevant information in some embodiments.

Additionally, relevant information may also include combinations of indications. For instance, some embodiments may provide biometric authentication procedures for some data sources. In such a case, the information provided by the data source and/or the coexistence of a biometrically confirmed submission may be relevant. As such, some embodiments of step 265 may access authentication data associated with CBT and/or at home device provided data. Some embodiments of method 250 may then proceed to step 270, 275 or directly to step 280.

At step 270, de-skewing and symmetrizing transforms are applied to ratio-scale and interval-scale variables, and at step 275, standardizing transformations may be applied to ratio-scale and interval-scale variables. Next at step 280, the predictive model is used to determine a prediction for the target subject's risk (or likelihood) for relapse. In an embodiment, step 280 further determines the risk for relapse over a future time frame, and in another embodiment, step 280 determines a risk for relapse and a probable time-to-relapse. Some embodiments of step 280 utilize the R-package prodlim or other computational service 126. At step 285, the determined risk and corresponding time-to-relapse (where determined) may be provided to an appropriate caregiver associated with the subject. In an embodiment, an alert may be issued; the prediction information may be utilized for automatically scheduling an intervention or otherwise modifying a care for the subject, such as increasing monitoring, pharmaceutical combinations, or reaching out to the subject, for example. In some embodiments, the prediction may be stored and compared against future risk-of-relapse predictions to determine whether a patient's risk has changed.

EXAMPLE REDUCTION TO PRACTICE

With reference now to FIGS. 3A-6C and continuing reference to FIGS. 2A and 2B, an example embodiment reduced to practice is now described. This example embodiment comprises a system and method for time series properties-based early detection of emergent recidivism or non-adherence. This example embodiment actually reduced to practice considers treatment for alcoholism after relapse following initial treatment, and in particular, large observational electronic health record (EHR) derived de-identified datasets, such as Cerner Health Facts® data warehouse, enable (a) discovery of patterns that denote incipient relapse or non-adherence and (b) the development of predictive mathematical models that predict relapse risk and time to relapse based on treatment rank-order. Further, this example embodiment, which was actually reduced to practice, represents a demonstrable improvement to the technological capabilities of decision support systems, electronic health records systems, and predictive medicine generally, through the performance of unconventional techniques, such as the techniques described in references to FIG. 2A and/or FIG. 2B. Further, at least part of the improvement realized through the embodiments described herein may be achieved through the unconventional arrangement of the analytical techniques and/or components used to develop the predictive model and facilitate the forecasting of relapse.

In this example reduced to practice, records were retrieved from a patient health records data warehouse, which is derived from Cerner electronic health records (EHR) from 100% of episodes of care that are incident upon the participating health institutions. The personally-identifiable information was removed in conformance with U.S. HIPAA law and regulations, and the de-identified data were stored in a separate, secure database. A total of 177,237 distinct outpatients cared for at 343 U.S. health institutions and having treatment episodes between 1 Jan. 2000 and 31 Dec. 2014 coded with alcohol dependency ICD-9 diagnoses in the 303.xx range were extracted from the Cerner Health Facts® data warehouse. The male-to-female ratio in this cohort was 1.97. All longitudinally-linked treatment episodes were retrieved, and CPT-4, HCPCS, and ICD-9 procedure codes were extracted for all patients in this cohort. A subgroup comprised of 1,031 patients in the cohort received all of treatment for alcohol dependency in the facility (HIPAA-covered entity) where they first presented for care and experienced a first relapse.

Figure 3A:
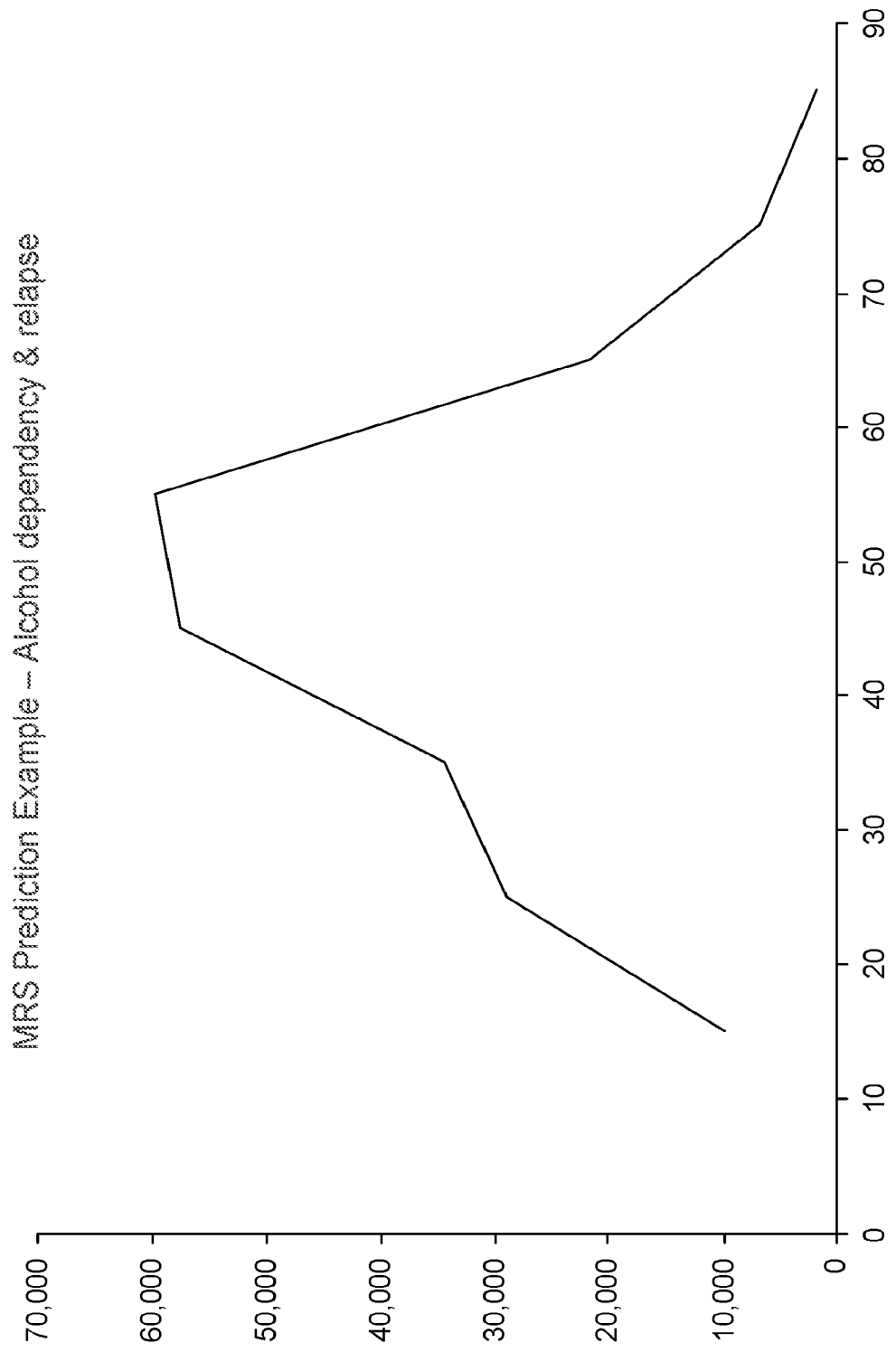
Figures 3B, 3C:
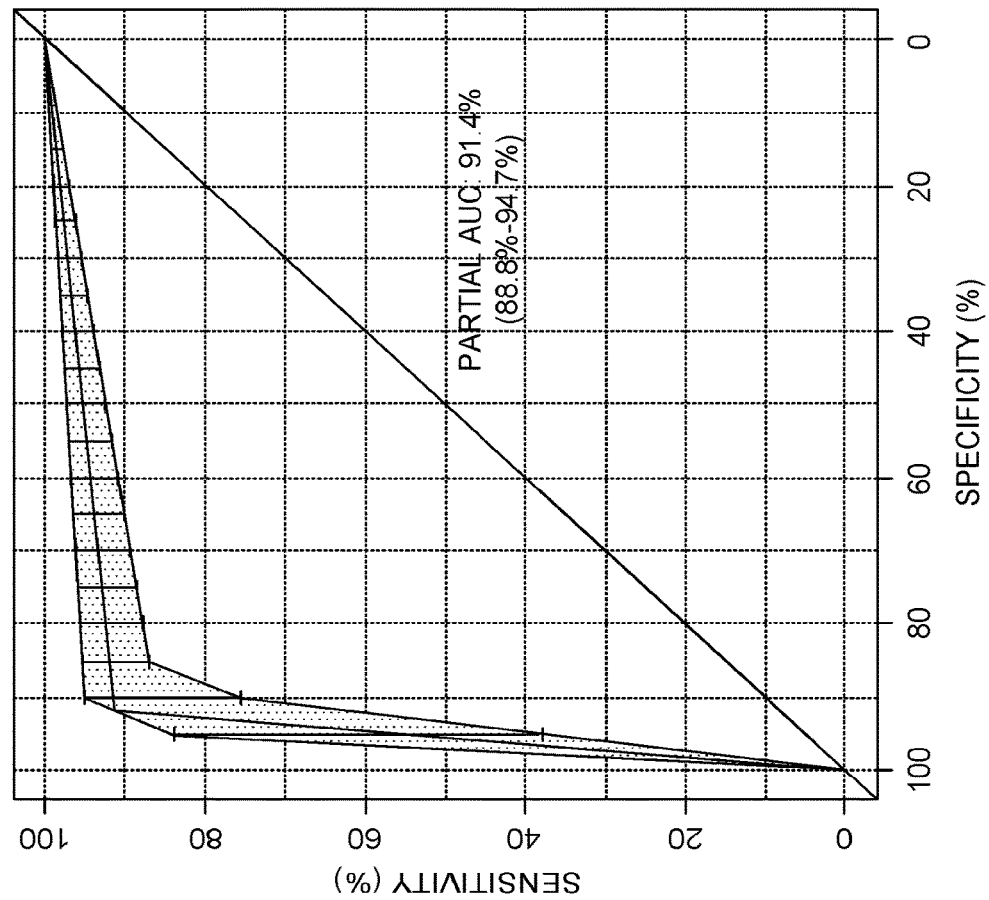

Subsequent to the first relapse, a subset of 408 patients in the subgroup received treatment for alcohol dependency in the same facility as previously, such that ascertainment of second relapse or later relapses was possible from the records available. Following de-skewing and standardization of the time-to-relapse #1 variable, Cox multiplicative relative survival regression was performed with the R package MRsury running on a Linux computer system. As shown in FIG. 3B, the Receiver Operating Characteristic (ROC) curve represents the accuracy and discriminating classificatory capacity of this example embodiment in the cohort of 408 subjects. The ROC area under the curve in the final composite model for the time series data set for the reduction to practice was 0.91. (See FIG. 3B, 3D which illustratively provides a computer program routine for generating the ROC of FIG. 3B, and corresponding statistics shown in FIG. 3C.) A run time version of the model was implemented in a Cerner Millennium® electronic health record system. FIG. 3A illustratively depicts an aspect of the multiplicative-regression model for relative survival (MRS) example for alcohol dependency & relapse. For reference, FIGS. 4A-4B show Kaplan-Meier survival curves for time to relapse 1 and time to relapse 2 events for alcohol dependency.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the following claims.

What is claimed is:

1. A method for predicting relapse or non-adherence in an individual subject based on a predictive model, the method comprising:
    selecting a cohort of historical subjects in an electronic health records system with known relapse statuses;
    retrieving for the selected cohort of historical subjects historical values for variables including one or more of treatment events, medication history, substance use history, demographic attributes, and laboratory tests;
    standardizing the retrieved historical values using one or more processors to symmetrize and deskew distributions of ratio-scale or interval-scale variables included inthe retrieved historical values;
    performing dimensionality reduction using Least Absolute Shrinkage and Selection Operator (LASSO) regression;
    based on the LASSO regression, determining a set of statistically-significant independent variables and a set of dependent variables from the symmetrized and deskewed distributions of ratio-scale or interval-scale variables;
    performing relative survival regression using multiplicative Cox Proportional Hazards relative survival regression of the set of dependent variables on the set of statistically-significant independent variables;
    storing the independent variables' regression coefficients determined by the relative survival regression thereby forming the predictive model for determining likelihood of addiction relapse or non-adherence;
    accessing the predictive model and corresponding model variables;
    accessing a health record information corresponding to the individual subject, and extracting subject values corresponding to the model variables from the health record information of the individual subject;
    standardizing the subject values using one or more processors to symmetrize and deskew ratio-scale or interval-scale values included in the subject values to generate a plurality of standardized values;
    utilizing the predictive model and the plurality of standardized values to determinea predicted likelihood of relapse for the individual subject;
    comparing the predicted likelihood of relapse with a predetermined threshold; and
    responsive to the predicted likelihood of relapse exceeding the predetermined threshold, automatically modifying a care plan for the individual subject and providing the determined likelihood of relapse prediction to a caregiver associated with the individual subject via a notification, wherein modifying the care plan comprises increasing monitoring, modifying a pharmaceutical combination administered to the individual subject, or scheduling a caregiver visit with the individual subject.

2. The method of claim 1, wherein the ratio-scale or interval-scale variables are standardized such that an arithmetic mean of each is zero and a standard deviation of each is equal to one.

3. The method of claim 1, wherein LASSO regression is performed with either an LI absolute-value penalty function or an L2 quadratic ridge penalty function.

4. The method of claim 1, wherein the notification comprises an alert, and wherein the threshold is pre-determined based on the individual subject.

5. The method of claim 1 wherein symmetrizing and de-skewing comprises applying a power-law.

6. The method of claim 1 wherein symmetrizing and de-skewing comprises applying a logarithmic transform.

7. A system for predicting relapse or non-adherence in an individual subject based on a predictive model, the system comprising:
    at least one processor; and
    non-transitory storage media including instructions that when executed by the at least one processor cause the at least one processor to perform operations comprising:
    selecting a cohort of historical subjects in an electronic health records system with known relapse statuses;
    retrieving for the selected cohort of historical subjects historical values for variables including one or more of treatment events, medication history, substance use history, demographic attributes, and laboratory tests;
    standardizing the retrieved historical values using one or more processors to symmetrize and deskew distributions of ratio-scale or interval-scale variables included inthe retrieved historical values;
    performing dimensionality reduction using Least Absolute Shrinkage and Selection Operator (LASSO) regression;
    based on the LASSO regression, determining a set of statistically-significant independent variables and a set of dependent variables from the symmetrized and deskewed distributions of ratio-scale or interval-scale variables;
    performing relative survival regression using multiplicative Cox Proportional Hazards relative survival regression of the set of dependent variables on the set of statistically-significant independent variables;
    storing the independent variables' regression coefficients determined by the relative survival regression thereby forming the predictive model for determining likelihood of addiction relapse or non-adherence;
    accessing the predictive model and corresponding model variables;
    accessing a health record information corresponding to the individual subject, and extracting subject values corresponding to the model variables from the health record information of the individual subject;
    standardizing the subject values, using one or more processors to symmetrize and deskew ratio-scale or interval-scale values included in the subject values to generate a plurality of standardized values;
    utilizing the predictive model and the plurality of standardized values to determinea predicted likelihood of relapse for the individual subject;
    comparing the predicted likelihood of relapse with a predetermined threshold; and
    responsive to the predicted likelihood of relapse exceeding the predetermined threshold, automatically modifying a care plan for the individual subject and providing the determined likelihood of relapse prediction to a caregiver associated with the individual subject via a notification, wherein modifying the care plan comprises increasing monitoring, modifying a pharmaceutical combination administered to the individual subject, or scheduling a caregiver visit with the individual subject.

8. The system of claim 7, wherein symmetrizing and de-skewing comprises applying a power-law.

9. The system of claim 7, wherein symmetrizing and de-skewing comprises applying a logarithmic transform.

10. The system of claim 7, wherein the ratio-scale or interval-scale variables are standardized such that an arithmetic mean of each is zero and the standard deviation of each is equal to one.

11. The system of claim 7, wherein LASSO regression is performed with either an LI absolute-value penalty function or an L2 quadratic ridge penalty function.

12. The system of claim 7, wherein the notification comprises an alert, and wherein the threshold is pre-determined based on the individual subject.

* * * * *